United States Patent
Ueda

(10) Patent No.: US 8,043,610 B2
(45) Date of Patent: Oct. 25, 2011

(54) FREEZE-DRIED COMPOSITION OF INACTIVATED VIRUS ENVELOPE WITH MEMBRANE FUSION ACTIVITY

(75) Inventor: Takafumi Ueda, Yokkaichi (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 0 days.

(21) Appl. No.: 12/582,115

(22) Filed: Oct. 20, 2009

(65) Prior Publication Data

US 2010/0040580 A1 Feb. 18, 2010

Related U.S. Application Data

(62) Division of application No. 11/629,289, filed as application No. PCT/JP2005/010720 on Jun. 10, 2005.

(30) Foreign Application Priority Data

Jun. 14, 2004 (JP) ................................. 2004-176105

(51) Int. Cl.
*A61K 48/00* (2006.01)
(52) U.S. Cl. ................. 424/93.1; 424/211.1; 424/209.1; 424/204.1
(58) Field of Classification Search .................. None
See application file for complete search history.

(56) References Cited

U.S. PATENT DOCUMENTS

| | | | |
|---|---|---|---|
| 5,631,237 A | 5/1997 | Dzau et al. | |
| 6,913,923 B2 | 7/2005 | Kaneda | |
| 7,504,098 B2 * | 3/2009 | Kaneda et al. | 424/93.1 |
| 2003/0202988 A1 * | 10/2003 | Chaplin et al. | 424/232.1 |
| 2004/0253272 A1 | 12/2004 | Kaneda | |

FOREIGN PATENT DOCUMENTS

| | | |
|---|---|---|
| DE | 299 213 | 4/1992 |
| EP | 0 872 249 | 10/1998 |
| EP | 1 170 363 | 1/2002 |
| EP | 1 420 065 | 5/2004 |
| JP | 57-95917 | 6/1982 |
| JP | 2000/502672 | 3/2000 |
| WO | 00/29024 | 5/2000 |
| WO | 00/34444 | 6/2000 |
| WO | 01/57204 | 8/2001 |
| WO | 03/014338 | 2/2003 |

OTHER PUBLICATIONS

Caldwell and Lyles. Interaction of Sendai Virus Proteins with the Cytoplasmic Surface of Erythroctye Membranes following Viral Envelope Fusion. J of Biological Chemistry. 1981. 256(10): 4838-4842.*
Dzau, V.J. et al., "Fusigenic Viral Liposome for Gene Therapy in Cardiovascular Diseases" Proc. Natl. Acad. Sci. USA, vol. 93, pp. 11421-11425, Oct. 1996.
Kaneda, Y. et al., "Gene Therapy Using HVJ-Liposomes: The Best of Both Worlds?"; Molecular Medicine Today, vol. 5, p. 298-303, Jul. 1999.

\* cited by examiner

*Primary Examiner* — Zachariah Lucas
*Assistant Examiner* — Michelle S Horning
(74) *Attorney, Agent, or Firm* — Oblon, Spivak, McClelland, Maier & Neustadt, L.L.P.

(57) ABSTRACT

The objects of the present invention are to provide a freeze-dried composition of an inactivated virus envelop having membrane fusion activity which can be stored at higher temperatures without losing the ability to introduce foreign matters and to provide a method of introducing a foreign matter into a cell with high efficiency.
The present invention provides a freeze-dried composition for introducing a foreign matter which comprises an inactivated virus envelope having membrane fusion activity, and at least one stabilizer selected from the group consisting of a protein hydrolysate, leucine, an L-arginine-acid and a polysaccharide, and a method of introducing a foreign matter using the freeze-dried composition containing an inactivated virus envelope.

12 Claims, No Drawings

FREEZE-DRIED COMPOSITION OF INACTIVATED VIRUS ENVELOPE WITH MEMBRANE FUSION ACTIVITY

Cross-Reference to Related Applications

This application is a divisional of U.S. Pat. No. 11/689,289 filed Dec. 23, 2006, pending, which is a 371 of PCT/JP05/10720 filed Jun. 10, 2005 and claims the benefit of JP 2004-176105 filed Jun. 14, 2004.

TECHNICAL FIELD

The present invention relates to a freeze-dried composition used for introduction of nucleic acid, protein or drugs into cells and living organisms, a process for its production and its use.

BACKGROUND ART

In recent years, various viral and nonviral (synthetic) vector systems have been developed to introduce foreign matters such as genes into cells or living organisms. In general, for intracellular gene delivery, viral vector systems can introduce foreign matters more effectively than nonvial vector systems. However, viral vectors can have cause problems due to simultaneous expression of essential genes of the parent virus, leaky expression of viral genes, immunogenicity and modification of the host genome structure. While nonviral vectors are less cytotoxic and immunogenic, nonviral vector systems have a problem that nonviral vectors cannot introduce genes as efficiently as some viral vectors because in nonviral vector systems, foreign matters are taken up by cells endocytotically.

To overcome this problem, a liposome having the membrane fusion activity of sendai virus (hemagglutinating virus of Japan: HVJ) called a hybrid vector, i.e., a HVJ-liposome complex, was proposed. The membrane fusion activity of the virus enables intracellular gene transfer into cells and living organisms. This technique is frequently used in animal experiments worldwide (patent document 1 and non-patent documents 1 and 2). The HVJ-liposome is constructed by fusing preliminarily UV-inactivated HVJ (inactivated HVJ envelope) with a liposome loaded with a protein, a chemical substance or a gene. However, in addition of preparation of the inactivated HVJ envelope, cumbersome steps such as preparation of the liposome and isolation of the HVJ-liposome after fusion are required.

Therefore, direct encapsulation of genes into an inactivated HVJ envelope was proposed (patent document 2). In this system, the gene to be introduced into cells are encapsulated in an inactivated HVJ envelope by freeze-thawing or surfactant treatment in the presence of the gene, and the envelope is brought into contact with the recipient cells to introduce the gene through membrane fusion. This relatively easy gene transfer system using the mass-producible inactivated HVJ envelope has been used for introduction of foreign matters into cells in many studies.

On the other hand, though the inactivated HVJ envelope can be cryopreserved (−70° C.) in suspension without losing its gene transfer ability, no reports have been made about its freeze-drying storage, presumably because freeze-drying spoils the function or structure of the inactivated HVJ envelope having membrane fusion activity. However, a freeze-dried composition of the inactivated HVJ envelope which can be stored at higher temperatures has been demanded in view of transportation and storage.

Patent Document 1: U.S. Pat. No. 5,631,237
Patent Document 2: WO01/57204
Non-patent Document 1: Dzau, V. J. et al. Proc. Natl. Acad. Sci. USA, 93, 11421-11425 (1996)
Non-patent Document 2: Kaneda, Y. et al. Molecular Medicine Today, 5, 298-303 (1999)

DISCLOSURE OF THE INVENTION

Problems that the Invention is to Solve

Therefore, it is an object of the present invention to provide a freeze-dried composition of an inactivated virus envelope having membrane fusion activity which can be stored at higher temperatures without losing the ability to introduce foreign matters. Another object of the present invention is to provide a method of introducing a foreign matter into a cell with high efficiency.

Means of Solving the Problems

The present inventors studied extensively in search for ways to freeze-drying the inactivated virus envelope having membrane fusion activity, and as a result, found that addition of protein hydrolysates and certain amino acids helps the inactivated virus envelope having membrane fusion activity retain its ability to introduce foreign matters. Further, they also found that decrease in salts is effective for retaining the ability of the inactivated virus envelope to introduce foreign matters into cells. The present invention has been accomplished on the basis of these findings. They also found that these treatments effectively prevent loss of the membrane fusion activity of the inactivated virus envelope. Further, they accomplished a novel method of introducing foreign matters using a freeze-dried composition of the resulting inactivated virus envelope having membrane fusion activity.

Namely, the present invention provides:

1. A freeze-dried composition comprising an inactivated virus envelope having membrane fusion activity, and at least one stabilizer selected from the group consisting of a protein hydrolysate, leucine, an L-arginine-acid and a polysaccharide.
2. The freeze-dried composition according to claim 1, wherein the inactivated virus envelope is an inactivated virus envelope of a virus of Paramyxoviridae, Orthomyxoviridae, Herpesviridae, Hepadnaviridae and Flaviviridae.
3. The freeze-dried composition according to claim 1 or 2, wherein the stabilizer is a protein hydrolysate and a polysaccharide.
4. The freeze-dried composition according to any one of 1 to 3, which is prepared by a process comprising a step (1) of mixing a suspension of the inactivated virus envelope having membrane fusion activity and the stabilizer and a step (2) of freeze-drying the mixture obtained in the step (1).
5. The freeze-dried composition according to 4, wherein the concentration of the inactivated virus envelope in the mixture obtained in the step (1) is such that the OD 0.1 to 7.0.
6. The freeze-dried composition according to 4 or 5, wherein the concentration of the protein hydrolysate, leucine or the L-arginine-acid in the mixture obtained in the step (1) is from 0.1 to 2.5%.
7. The freeze-dried composition according to any one of 4 to 6, wherein the concentration of the polysaccharide in the mixture obtained in the step (1) is from 0.05 to 0.5%.
8. The freeze-dried composition according to any one of 4 to 7, wherein the salt concentration in the mixture obtained in the step (1) is at most 3 mM.

9. A method of introducing a foreign matter into a cell or a living organism, which comprises:
   (1) a step of rehydrating a freeze-dried composition containing an inactivated virus envelope having membrane fusion activity with a mixture comprising the foreign matter and water, and
(2) a step of bringing the composition obtained in the step (1) into contact with the cell or the living organism.
10. The method of introducing a foreign matter according to 9, wherein the freeze-dried composition is the freeze-dried composition as defined in any one of 1 to 8.
11. A cell fusion method comprising:
(a) step of rehydrating a freeze-dried composition containing an inactivated virus envelope having membrane fusion activity; and
(b) step of mixing the composition obtained in the step (a) with a suspension of cells to be fused.
12. The cell fusion method according to 11, wherein the freeze-dried composition is the freeze-dried composition as defined in any one of Claims 1 to 8.

EFFECTS OF THE INVENTION

The inactivated virus envelopes having membrane fusion activity reported so far have to be stored in a freezer (−20° C.), preferably in an ultracold freezer (−70° C. or below). For example, the inactivated HVJ envelope can substantially lose its ability to introduce foreign matters during about two weeks of refrigeration, and therefore, it is hardly storable in a place without freezing or ultracold freezing equipment and cannot stand a long time of transportation. The freeze-dried composition of an inactivated virus envelope having membrane fusion activity of the present invention is storable at room temperature (25° C. or below), easy to handle and free of restrictions on the place of use or transportation. Further, the method of introducing a foreign matter of the present invention drastically improves the transfer efficiency, is easier and finds widespread applications such as high throughput analyses.

BEST MODE FOR CARRYING OUT THE INVENTION

In the present invention, "inactivation", when referred to viruses, means inactivation of genes, and an inactivated virus can no longer replicate its genes and has lost its proliferation potency and infectivity. Virus inactivation is carried out by UV irradiation, irradiation of radioactive rays or treatment with an alkylating agent, preferably by UV irradiation or treatment with an alkylating agent, specifically speaking in accordance with WO01/57204, in particular by treatment with an alkylating agent. A virus envelope is generally consists of small spike-like structures made of spike proteins encoded by the virus gene and a lipid bilayer derived from the host and does not have proliferation potency itself. The spike proteins constituting the small spikes contain a membrane fusion protein which functions to confer the membrane fusion activity. In the present invention, "an inactivated virus envelope" comprehensively means an inactivated virus and/or its envelope. In the present invention, "an inactivated virus envelope having membrane fusion activity" means an inactivated virus envelope having a functional membrane fusion protein having membrane fusion activity.

Viruses having an envelope containing a membrane fusion protein include higher viruses of Paramyxoviridae, Orthomyxoviridae, Herpesviridae, Hepadnaviridae and Flaviviridae. These viruses utilize their membrane fusion activity to infect various cells through fusion with the plasma membranes of the cells. In the present invention, any virus that show such a property may be used. Therefore, it is preferred to use a virus of Paramyxoviridae, Orthomyxoviridae, Herpesviridae, Hepadnaviridae or Flaviviridae, preferably a virus of Paramyxoviridae, particularly preferably HVJ (Sendai virus).

Cultivation of the above-mentioned viruses is described in "Protocols for Virus Experiments: 1995 published by Medical View Co., Ltd." For example, Sendai virus of the Paramyxoviridae family can be proliferated in chicken fertilized eggs or by persistent infection in mammalian cell or tissue cultures (containing a hydrolase such as trypsin).

For preparation of the inactivated virus envelope having membrane fusion activity, ultracentrifugation, isolation by column chromatography, reconstitution and the like are available. Isolation is preferably carried out by ion chromatography, specifically as described in Example 1 (1) and Examples 7 (1) to (5) of WO03/014338.

In the case of isolation by ion chromatography, the inactivated virus envelope is eluted with a high concentration buffer solution from ion chromatography, and then, concentrated, for example, dialytically by means of a tangential-flow filter (TFF) module repeatedly so as to give a suspension of the inactivated virus envelop which will have a concentration corresponding to an OD (turbidity at 558 nm, unless otherwise noted) of from 0.1 to 7.0, preferably from 0.25 to 5.0, particularly preferably from 0.3 to 2.5, after mixed with a stabilizer in the subsequent step. The final concentration of salts such as the buffering agent and NaCl in the mixture of the suspension of the inactivated virus envelop with the stabilizer is adjusted to at most 3 mM, preferably at most 1 mM, particularly preferably at most 0.3 mM.

When the inactivated virus envelope is prepared by ultracentrifugation or reconstitution, the final salt concentration is adjusted to at most 3 mM, preferably at most 1 mM, particularly preferably at most 0.3 mM.

In the present invention, the protein hydrolysate to be used as the stabilizer may be polypeptone, bactopeptone, bactotryptone or a casein acid-hydrolysate, preferably polypeptone, bactopeptone or a casein acid-hydrolysate, particularly preferably polypeptone or bactopeptone. The amino acid to be used as the stabilizer may be L-leucine or an L-arginine monohydrochloride, preferably an L-arginine monohydrochloride. To dissolve the protein hydrolysate, leucine or an L-arginine-acid, a solvent such as distilled water, UF water or a buffer solution, preferably distilled water or UF water, is used. The protein hydrolysate, leucine or the L-arginine-acid is added at a concentration of from 0.1% to 2.5%, preferably 0.2% to 1.5% to a suspension of the inactivated virus envelope before freeze-drying.

In the present invention, the polysaccharide to be used as the stabilizer may be, for example, methyl cellulose, β-glucan, pectin, agarose, dextrin or dextran, preferably methyl cellulose. To dissolve the polysaccharide, a solvent such as distilled water, UF water or a buffer solution, preferably distilled water or UF water, is used. The polysaccharide is added at a concentration of from 0.05% to 0.5%, preferably from 0.1% to 0.2% to the suspension of the inactivated virus envelope before freeze-drying. Addition of a polysaccharide makes the resulting freeze-dried composition easier to handle by suppressing dusting. A similar antidusting effect can be achieved by addition of trehalose.

One or more stabilizers selected from the group consisting of protein hydrolysates, amino acids and polysaccharides may be used singly or in combination of two or more. The combined use of a protein hydrolysate with a polysaccharide or the combined use of an amino acid with a polysaccharide is preferred. The combined use of a protein hydrolysate with a polysaccharide, specifically the combined use of polypeptone or bactopeptone and methyl cellulose, is particularly preferred.

The freeze-dried composition of the present invention is prepared, for example, by adding a protein hydrolysate, an amino acid or a polysaccharide at a predetermined concentration, and optionally adding a known pH adjusting agent, a known isotonicity agent, a known stabilizer or a known preservative, to the virus envelope having membrane fusion activity prepared as described above. The protein hydrolysate, the amino acid or the polysaccharide may be dissolved in the above-mentioned aqueous solvents respectively before added at predetermined concentrations to the virus envelope having membrane fusion activity. The resulting mixture is freeze-dried by ordinary methods. For the freeze-drying, a know method such as tray freeze-drying, spray freeze-drying or vial freeze-drying under ordinarily used conditions may be used.

The freeze-dried composition of an inactivated virus envelope having membrane fusion activity covers the followings.
(A) A freeze-dried composition for introducing a foreign matter, which comprises an inactivated virus envelope having membrane fusion activity, and at least one stabilizer selected from the group consisting of a protein hydrolysate, leucine, an L-arginine-acid and a polysaccharide, which is prepared by a process comprising
a step (1) of mixing a suspension of the inactivated virus envelope having membrane fusion activity and the stabilizer; and
a step (2) of freeze-drying the mixture obtained in the step (1);
(B) The freeze-dried composition according to (A), wherein the concentration of the inactivated virus envelope in the mixture obtained in the step (A)(1) corresponds to an OD (Optical Density) of from 0.1 to 7.0, and the concentration of the protein hydrolysate in the mixture obtained in the step (A)(1) is from 0.1% to 2.5%;
(C) The freeze-dried composition according to (A), wherein the concentration of the inactivated virus envelope in the mixture obtained in the step (A)(1) corresponds to an OD of from 0.1 to 7.0, and the concentration of the polysaccharide in the mixture obtained in the step (A)(1) is from 0.05 to 0.5%;
(D) The freeze-dried composition according to (A), wherein the concentration of the inactivated virus envelope in the mixture obtained in the step (A)(1) corresponds to an OD of from 0.1 to 7.0, the concentration of the protein hydrolysate in the mixture obtained in the step (A)(1) is from 0.1% to 2.5%, and the concentration of the polysaccharide in the mixture obtained in the step (A)(1) is from 0.05 to 0.5%; and
(E) The freeze-dried composition according to any one of (A) to (D), wherein the salt concentration in the mixture obtained in the step (1) is at most 3 mM.

The freeze-dried composition of the present invention can be used to prepare a transfer vector by loading a foreign matter into an inactivated virus envelop having membrane fusion activity. The transfer vector for introducing a foreign matter is added or administered into cells or a living organism to introduce the foreign matter. It was found that rehydration is available as a novel method of preparing the vector for introducing a foreign matter.

Rehydration does not use any surfactants which are conventionally necessary, and a freeze-dried composition containing an inactivated virus envelope having membrane fusion activity is rehydrated, for example, by mixing it with an aqueous solution or suspension of a foreign matter. The foreign matter can be introduced by adding or administering the rehydrated freeze-dried composition immediately after the rehydration, preferably after from 0 to 10 minutes of incubation at 0° C. to 25° C. In the case of a large number of samples, the incubation may be extended for another couple of hours. The concentrations and the mixing ratio can be selected arbitrarily without any particular restrictions. The concentration of the inactivated virus envelop having membrane fusion activity corresponds to an OD of from 0.05 to 5.0, preferably an OD of from 0.05 to 2.0, particularly preferably an OD of from 1.0 to 2.0. For example, when the foreign matter is DNA, its concentration is from 0.02 to 40 μg/μl, preferably from 0.2 to 10 μg/μl. The inactivated virus envelope having membrane fusion activity after aging carries the foreign matter and serves as a vector for introducing the foreign matter. This method is quite different from the freeze-thawing method comprising repetitive freezing and thawing.

It is possible to prepare a vector for introducing a foreign matter from the freeze-dried composition of the present invention by a conventional method using surfactants. In the surfactant method, the freeze-dried composition is rehydrated with PBS (−) (phosphate buffered saline) or a gene transfer medium which does not contain the foreign matter to be introduced to make a suspension containing the inactivated virus envelope at a concentration corresponding of an OD of from 0.1 to 1.0, and then the suspension is mixed with an aqueous solution or suspension of the foreign matter to be introduced. To the resulting mixture, a surfactant such as Triton X-100 is added at a concentration of 0.001% to 0.5%, preferably from 0.05% to 0.3%, and the resulting mixture is allowed to stand for several seconds to several hours, preferably from 3 to 10 minutes, at a low temperature, preferably at from 0° C. to 25° C., particularly preferably at from 0° C. to 4° C. Then, the surfactant is removed by centrifugation to obtain a vector for introducing a foreign matter.

In the present invention, the foreign matter to be introduced into cells or a living organism is usually a drug or a gene, though there are no particular restrictions. Specific examples include antibiotics, chemotherapeutic drugs, antiallergic drugs, cardiovascular drugs, anti-inflammatory drugs, antirheumatic drugs, hormones, vitamins, antineoplastic drugs, ribo-contrast media, magnetic resonance contrast media, biologically active proteins and nucleic acids. Specifically, when a nucleic acid is used, it may be selected from a nucleic acid encoding a protein of interest which can be expressed into the protein of interest in cells, a ribozyme, an antisense nucleotide, a DNA which expresses an RNA which induces RNAi, an siRNA, a suicide gene and an apoptosis-inducing gene and the like. It is possible to construct a vector for introducing foreign matters which carries one of these foreign matters or two or more of them. As the foreign matter, a nucleic acid, particularly a nucleic acid encoding a protein of interest which can be expressed into the protein of interest in cells, is preferable.

When protamine sulfate is used for introduction of a foreign matter such as a nucleic acid into cells or a living organism, the mixture of the nucleic acid and the inactivated virus envelope is diluted with PBS(−) or a gene transfer medium to a nucleic acid concentration of at most 0.1 μg/μl after incubation, to prevent the nucleic acid from coprecipitating with protamine sulfate added later. The resulting solution is added to cultured cells directly or after addition of protamine sulfate. Protamine sulfate is added at a concentration of from 1 μg/ml to 100 μg/ml, preferably 10 μg/ml to 50 μg/ml. When protamine sulfate is not used, the above operation is not necessary.

In the present invention, the cells as the target for introduction of the foreign matter are eukaryotic cells, especially animal cells, and may be adherent cells or suspension cells. It is applicable to a wide variety of cell lines including generally difficult target cells such as primary cultured cells, stem cells, fibroblasts and macrophages. The vector for introducing foreign matters is added to a culture of these cells and brought into contact with them. The vector for introducing foreign matters of the present invention may be administered in vivo or systemically, namely through a route appropriate for the disease to be treated, the target organ or the like, for example, intravenously, intraarterially, subcutaneously or intramuscularly, or directly to a diseased region such as the kidney, the liver, the lung, the brain or the nerve. Direct administration to diseased regions allows organ-specific therapy. Under ordinary cell culture conditions or feeding conditions, the foreign matter is introduced into cells a certain time after the addition or administration of the vector. It may be administered ex vivo by an ordinary method by collecting mammalian cells (such as lymphocytes or hematopoietic stem cells) and sensitizing them with the vector for introducing foreign matters of the present invention and then returning the cells to the mammalian body.

The cells as the target of cell fusion are animal cells, preferably mammalian cells, such as immunocytes, bone marrow cells, dendritic cells, blood cells, embryonic stem cells, tissue stem cells, neuronal cells, glial cells, pituitary cells, hepatocytes, pancreatic cells, renal cells, cardiomyocytes, muscular cells, osteoblasts, chondrocytes, adipocytes, vascular endothelial cells, fibroblasts or cancer ells such as myeloma cells, HeLa cells, CHO cells, COS cells. Cell fusion of these cells may be carried out between different types of cells, for example, immunocytes and cancer cells. Further, the freeze-dried composition of the present invention may be used for nuclear replacement or fusion between micronuclei and the target cells.

In the present invention, when the target cells are fused, the cell density is from $1 \times 10^4$ cells/ml to $1 \times 10^{10}$ cells/ml, preferably from $1 \times 10^6$ cells/ml to $1 \times 10^8$ cells/ml, and the Ca concentration is from 0.1 to 10 mM, preferably from 1 to 5 mM.

Now, the present invention will be described in reference to Examples. However, these specific Examples are mere embodiments which illustrate and by no means define or restrict the scope of the invention disclosed in the present application. It should be understood that the present invention covers various embodiments based on the concept disclosed in the application.

EXAMPLES

Example 1

120 µl of an inactivated HVJ envelope, GenomOne (registered trademark, Ishihara Sangyo Kaisha, Ltd.) (OD: 0.25, amount: 6000 HAU) was put into vials and centrifuged at 10,000 rpm for 30 minutes, and the supernatants were removed. The resulting precipitates were washed by suspending them in 40 µl of distilled water, centrifuging the suspensions again at 10,000 rpm for 30 minutes and removing the supernatants. The precipitates were suspended in 60 µl of a 0.2% polypeptone solution in distilled water (Sample 1, and similar references will be made hereinafter), a 0.2 mannitol solution in distilled water (Sample 2), a 0.2% methyl cellulose solution in distilled water (Sample 3) or a 0.2% trehalose solution in distilled water (Sample 4), and the suspensions were frozen quickly in liquid nitrogen.

Frozen Samples 1 to 4 were freeze-dried in a vacuum of at most 0.1 mmHg at a trap temperature of at most −70° C. for 5 hours in a vacuum desiccator under temperature control by soaking in a cooling bath set at −15° C. Secondary drying was carried out for another one hour at a higher cooling bath temperature of 4° C. Dry nitrogen was introduced into the vacuum chamber to break the vacuum, and then, the vials were sealed. Thus, samples of freeze-dried compositions were obtained.

Samples freeze-dried in the absence of methyl cellulose or trehalose rose in clouds, probably electrostatically, upon sealing or opening of the vials, and had to be handled carefully. Addition of methyl cellulose or trehalose suppressed such dusting.

Example 2

From 120 µl portions of GenomOne (registered trademark, Ishihara Sangyo Kaisha, Ltd.) (OD: 0.25, amount: 6000 HAU), precipitates were prepared in the same manner as in Example 1. The precipitates were suspended in 60 µL of a 0.5% polypeptone solution in distilled water (Sample 5, and similar references will be made hereinafter), a 0.5% polypeptone and 0.1% methyl cellulose solution in distilled water (Sample 6), a 1.0% polypeptone and 0.1% methyl cellulose solution in distilled water (Sample 7), a 1.5% polypeptone and 0.1% methyl cellulose solution in distilled water (Sample 8) or a 2.5% polypeptone and 0.1% methyl cellulose solution in distilled water (Sample 9), and the suspensions were frozen quickly in liquid nitrogen.

From the subsequent step, Example 1 was followed to obtain Samples 5 to 9 of freeze-dried compositions.

Example 3

From 120 µl portions of GENOMONE™ (Ishihara Sangyo Kaisha, Ltd.) (OD: 0.25, amount: 6000 HAU), precipitates were prepared in the same manner as in Example 1. The precipitates were suspended in 60 µL of a 1.0% polypeptone solution in distilled water (Sample 10, and similar references will be made hereinafter), a 1.0% bactopeptone solution in distilled water (Sample 11), a 1.0% bactotriptone solution in distilled water (Sample 12), a 1.0% casein acid-hydrolysate in distilled water (Sample 13), a 0.3% L-leucine solution in distilled water (Sample 14), a 1.0% β-alanine solution in distilled water (Sample 15), a 0.3% L-arginine monohydrochloride in distilled water (Sample 16) or a 1.0% L-aspartic acid solution in distilled water (Sample 17), each containing 0.1% methyl cellulose, and frozen quickly in liquid nitrogen. From the subsequent step, Example 1 was followed to obtain Samples 10-17 of freeze-dried compositions.

Example 4

Preparation of pCMV-GL3

The plasmid DNA of pGL3-CONTROL VECTOR (Promega Co.) encoding a modified firefly luciferase protein was cleaved with Hind III and Xba I and electrophoresed (1% agarose), and the fragment containing luciferase was isolated by means of Gel-M Extraction System (VIOGENE Inc.). Similarly, PcDNA 3.1(+) vector containing CMV promoter (Invitrogene Co.) was cleaved, and a fragment containing the CMV promoter region was isolated. The two fragments were ligated by means of DNA Ligation Kit (TaKaRa Bio Inc.) and transformed into *E. coli* (DH5α) (45° C., 45 minutes). The Ampicillin-resistant cells containing pCMV-GL3 plasmid DNA expressing luciferase under control by CMV promoter were selected.

The selected cells were incubated in LB medium (containing ampicillin), and the cell culture was purified by means of EndoFree Plasmid Giga Kit (QIAGEN Inc.). The purification product was dissolved in TE buffer to give a pCMV-GL3/TE solution.

Example 5

Conventional Gene Transfer

Each of Samples 1 to 17 of freeze-dried compositions obtained in Examples 1 to 3 was dispersed in 120 μl of a buffer (PBS(−)), and 20 μl of each dispersion was dispensed into an eppendorf tube and centrifuged at 10,000 for 5 minutes. The supernatants were removed, and the precipitates were suspended in 5 μl of PBS(−). After addition of 5 μl of 4 μg/μl pGL3/TE and 1 μl of 2% Triton X-100/PBS(−), the suspensions were centrifuged at 10,000 for 5 minutes. The supernatants were removed, and the precipitates were suspended in 15 μl of PBS(−). After addition of 2.5 μl of 10 mg/ml protamine sulfate/PBS(−), the suspensions were added to a HeLa S3 cell culture (24-well dish, $6 \times 10^4$ cells/dish, 0.5 ml DMEM, 10% FCS), and the cell culture was incubated at 37° C. in 5% $CO_2$ for 24 hours.

After incubation, the culture medium was removed, and 100 μl of PBS(−) was added. 100 μl of Lyophilized Substrate Solution of a luciferase assay kit Luclite (Perkin Elmer Inc.) was added to lyse the cells, and the luciferase activities (fluorescence intensities) were measured by means of fluorescence/luminescence/absorbance-multi-function reader GENios (TECAN). The test results are shown in Table 1.

Example 6

Preparation of Freeze-Dried Compositions of an Inactivated HVJ Virus Envelope Having Membrane Fusion Activity For preparation of an inactivated HVJ virus envelope to be used, the procedures in Example 1(1) and Example 7(1) to (4) of WO03/014338 were followed until the inactivated HVJ envelope suspension was obtained after the buffer exchange. In short, HVJ was proliferated in fertilized chicken eggs, inactivated by β-propiolactone treatment, then pretreated (filtration), concentrated and subjected to column chromatography (Q Sepharose FF) to collect a 10 L of a column fraction containing the inactivated HVJ envelope. The column fraction was concentrated to 100 ml through a tangential flow filter (TFF) module. 100 mL of the concentrate was combined with 100 ml of a buffer (20 mM Tris-HCl (pH 7.5), 150 mM NaCl, 1 mM MgCl2) and further concentrated to 100 ml. This operation (buffer exchange) was performed twice.

The inactivated HVJ envelope suspension obtained after the buffer exchange was diluted with sterilized water to 500 ml and concentrated to 100 ml through the TFF module. The dilution with sterilized water and the TFF concentration were repeated five times to obtain 60 ml of a concentrate. To the concentrate, 25 ml of a sterilized aqueous solution containing 4.0% polypeptone and 0.4% methyl cellulose was added. The concentration of the resulting inactivated HVJ envelope suspension containing stabilizers corresponded to an OD of 0.6. After the concentration, the buffer concentration had been reduced to 0.03 mM or below. The suspension was dispensed in 65 μl aliquots into 1.5 ml screw-capped tubes and frozen quickly in liquid nitrogen. The frozen inactivated HVJ envelope suspension was freeze-dried in a vacuum of at most 0.1 mmHg at a trap temperature of at most −70° C. for 15 hours in a vacuum chamber set at −15° C. Secondary drying was carried out for another one hour at a higher vacuum chamber temperature of 4° C. Dry nitrogen was introduced into the vacuum chamber to break the vacuum, and the tubes were sealed.

Example 7

Gene Transfer by Rehydration

The freeze-dried composition of the inactivated HVJ envelope (freeze-dried product) obtained in Example 6 was dispersed in 30 μl of 4 μg/μl pCMV-GL3/TE solution, 120 μl of 1 μg/μl pGL3/TE solution or 480 μl of 0.25 μg/μl pGL3/TE solution prepared in accordance with Example 4 and allowed stand still on ice for 5 minutes. 450 μl or 360 μl of a buffer (PBS(−)) was added to a total volume of 480 μl, and the 15 μl of 10 mg/ml protamine sulfate/PBS(−) was added. The resulting solutions were inoculated in 40 μl aliquots onto a CHO-K1 cell culture (Chinese hamster ovary cells, ATCC NO. CCL-61, purchased from Dainippon Pharmaceutical Co., Ltd.) in a 24-well plate ($2.5 \times 10^4$ cells/well, Ham's F12+10% FCS 0.5 ml/well, incubated at 37° C. in 5% $CO_2$ overnight) and incubated at 37° C. in 5% $CO_2$ for 24 hours.

The culture medium was removed, and 125 μl of PBS(+) was added. The cells were lysed with 125 μl of Substrate Solution of a luciferase assay kit Luclite (Perkin Elmer Inc.). The luciferase activities (fluorescence intensities) in 50 μl of the cell lysates were measured by means of MICROPLATE SCINTILLATION & LUMINESCENCE COUNTER, Topcount (PACKARD).

For comparison, an experiment was carried out with an inactivated HVJ envelope vector prepared by a conventional method using a surfactant. 40 μl of an inactivated HVJ envelope suspension (referred to as a conventional product) in accordance with Example 1(1) and Example 7(1) to (5) of WO03/013348 (equivalent in amount to ⅓ of the inactivated HVJ envelope in the freeze-dried product obtained in Example 6) was put into a 1.5 mL microtube and centrifuged at 10,000 for 5 minutes. The supernatant was removed, and the precipitate was suspended with 10 μl of PBS(−). After addition of 10 μl of 4 μg/μl pCMV-GL3/TE and 2 μl of 2% Triton X-100/PBS(−), the suspension was centrifuged at 10,000 for 5 minutes. The supernatant was removed, and the precipitate was suspended with 30 μl of PBS(−), and then mixed with 5 μl of 10 mg/ml protamine sulfate/PBS(−). 8 μl of the resulting suspension was inoculated onto a CHO-K1 cell culture and incubated for 24 hours. Then, the luciferase activity was measured as described above.

The results are shown in Table 2 (averages in triplicate). The freeze-dried compositions of the present invention (referred to as freeze-dried products in Table 2) dispersed in a solution of a foreign gene transferred the foreign gene about 10 times as efficiently as the surfactant treated-inactivated HVJ envelope encapsulating the foreign gene prepared by a conventional method (referred to as the conventional product in Table 2).

Example 8

Preparation of a Freeze-Dried Composition of an Inactivated HVJ Envelope Having Membrane Fusion Activity For preparation of an inactivated HVJ virus envelope to be used, the procedures in Example 1(1) and Example 7(1) to (4)

of WO03/014338 were followed until the inactivated HVJ envelope suspension was obtained after the buffer exchange. In short, HVJ was proliferated in fertilized chicken eggs, inactivated by β-propiolactone treatment, then pretreated (filtration), concentrated and subjected to column chromatography (Q Sepharose FF) to collect a 5 L of a column fraction containing the inactivated HVJ envelope. The column fraction was concentrated to 200 ml through a tangential flow filter (TFF) module. 200 mL of the concentrate was combined with 200 ml of a buffer (20 mM Tris-HCl (pH 7.5), 150 mM NaCl, 1 mM MgCl2) and further concentrated to 200 ml. This operation (buffer exchange) was performed twice, and the resulting suspension was filtered using MILLIPAK™200 (0.45 μm, MILLIPORE Co.).

The inactivated HVJ envelope suspension obtained after the buffer exchange was diluted with sterilized water to 600 ml and concentrated to 200 ml through the TFF module. The dilution with sterilized water and the TFF concentration were repeated eight times to obtain 100 ml of a concentrate. To the concentrate, 26 ml of a sterilized aqueous solution containing 5.0% polypeptone and 0.5% methyl cellulose was added. The concentration of the resulting inactivated HVJ envelope suspension containing stabilizers corresponded to an OD of 0.6. After the concentration, the buffer concentration had been reduced to 0.03 mM or below. The suspension was dispensed in 210 μl aliquots into 1.5 ml screw-capped tubes and frozen quickly in liquid nitrogen. The frozen inactivated HVJ envelope suspension was freeze-dried in a vacuum of at most 0.1 mmHg at a trap temperature of at most −70° C. for 15 hours in a vacuum chamber set at −5° C. Secondary drying was carried out for another one hour at a higher vacuum chamber temperature of 5° C. Dry nitrogen was introduced into the vacuum chamber to break the vacuum, and the tubes were sealed.

Example 9

Cell Fusion Assay

The cell fusion activities of an inactivated HVJ envelope suspension prepared from the freeze-dried composition of the present invention obtained in accordance with Example 8 and, as a comparative example, a cryopreserved inactivated HVJ envelope obtained in accordance with Example 1 of WO03/013348 were assayed. The cell fusion activities were assayed in accordance with K. Hiraoka et al. (The Journal of Immunology, vol. 173, pp. 4297-4307). Namely, a Syrian baby hamster kidney cell line BHK-21 (purchased from Dainippon Pharmaceutical Co., Ltd.) stained with a fluorescent staining kit PKH26 (SIGMA-Aldrich Inc., No. PKH-26-GL, red fluorescence) or PKH67 (SIGMA-Aldrich Inc., No. PKH-67-GL, green fluorescence) was suspended in a cell fusion buffer (10 mM Tris-HCL (pH 7.5), 137 mM NaCl, 5.5 mM KCl, 2 mM $CaCl_2$) at $8 \times 10^6$ cells/ml. 25 μL of the cell suspensions stained with both dyes were mixed in a 2 mL microtube. The resulting mixture was mixed with 3 μL of inactivated HVJ envelope suspensions at given concentrations (OD 560 nm) in a buffer (PBS(−)), allowed to stand on ice for 5 minutes and incubated in a thermostat at 37° C. for 15 minutes (with tapping once at 5 minute intervals) to induce cell fusion. Subsequently, 300 μL of ice-cold PBS(+) buffer containing 1% BSA was added, and the ratio of double-positive cells emitting both red and green fluorescence was measured by means of Flow cytometer (FACSCalibur™, Becton Dickinson). For background measurement, a similar assay was carried out using a control group treated in the same manner except that a buffer (PBS(−)) was added instead of the inactivated envelop suspension, and the measured values were corrected for the respective groups. The fusion efficiency was calculated from the following equation.

Fusion efficiency (%)=(the number of double-positive cells in a treated group)/(the total number of cells in a treated group)×100−(the number of double-positive cells in the control group)/(the total number of cells in the control group)×100

The results are shown in Table 3 (values measured with two lots were averaged for both the freeze-dried composition of the present invention and the comparative example). The freeze-dried composition of the present invention showed a higher fusion efficiency than the comparative example.

TABLE 1

| | Stabilizer | | Luciferase activity |
| --- | --- | --- | --- |
| Sample | Protein hydrolysate or amino acid | Saccharide | (TOP COUNT) |
| 1 | 0.2% polypeptone | — | 10568 |
| 2 | — | 0.2% mannitol | 1337 |
| 3 | — | 0.2% methyl cellulose | 5421 |
| 4 | — | 0.2% trehalose | 3762 |
| 5 | 0.5% polypeptone | — | 8629 |
| 6 | 0.5% polypeptone | 0.1% methyl cellulose | 9820 |
| 7 | 1.0% polypeptone | 0.1% methyl cellulose | 15248 |
| 8 | 1.5% polypeptone | 0.1% methyl cellulose | 6065 |
| 9 | 2.5% polypeptone | 0.1% methyl cellulose | 4562 |
| 10 | 1.0% polypeptone | 0.1% methyl cellulose | 9810 |
| 11 | 1.0% bactopeptone | 0.1% methyl cellulose | 11075 |
| 12 | 1.0% bactotryptone | 0.1% methyl cellulose | 4529 |
| 13 | 1.0% casein acid-hydrolysate | 0.1% methyl cellulose | 8254 |
| 14 | 0.3% L-leucine | 0.1% methyl cellulose | 6620 |
| 15 | 1.0% β-alanine | 0.1% methyl cellulose | 1819 |
| 16 | 0.3% L-arginine monohydrochloride | 0.1% methyl cellulose | 8086 |
| 17 | 1.0% L-aspartic acid | 0.1% methyl cellulose | 2049 |

TABLE 2

| Inactivated HVJ envelope used in gene transfer test | At the time of contact with DNA | | | DNA (μg) introduced into cultured cells per well | Luciferace activity (fluorescence intensity: TOP COUNT) | S.D. |
| --- | --- | --- | --- | --- | --- | --- |
| | Inactivated HVJ envelop concentration (OD) | DNA concentration (μg/μL) | Volume of the mixture (μL) | | | |
| Freeze-dried product | 1.3 | 4 | 30 | 9.69 | 132733 | 9488 |
| Freeze-dried product | 0.325 | 1 | 120 | 9.69 | 94584 | 11288 |
| Freeze-dried product | 0.082 | 0.25 | 480 | 9.69 | 83233 | 3978 |
| Conventional product | 0.59 | 1.8 | 22 | 9.14 | 11365 | 12704 |

TABLE 3

| | Fusion efficiency Concentration (OD) of inactivated HVJ envelope suspension | | |
| --- | --- | --- | --- |
| | 0.20 | 0.10 | 0.05 |
| The composition of the present invention | 10.1% | 15.4% | 13.2% |
| Comparative Example | 9.0% | 2.7% | 3.2% |

INDUSTRIAL APPLICABILITY

The freeze-dried composition of an inactivated virus envelope having membrane fusion activity of the present invention is storable at room temperature (25° C. or below) easy to handle and free of restrictions on the place of use or transportation. Further, the method of introducing a foreign matter of the present invention drastically improves the transfer efficiency, is easier and finds widespread applications such as high throughput analyses.

The entire disclosure of Japanese Patent Application No. 2004/176105 filed on Jun. 14, 2004 including specification, claims, drawings and summary is incorporated herein by reference in its entirety.

The invention claimed is:

1. A method of introducing foreign matter into a cell or a living organism, which method comprises:
   (1) rehydrating a freeze-dried composition containing an inactivated virus envelope having membrane fusion activity with a mixture comprising the foreign matter and water, wherein the inactivated virus envelope has membrane fusion activity, and at least one stabilizer selected from the group consisting of a protein hydrolysate, leucine, an L-orginine-acid and a polysaccharide, which is prepared by a process comprising (I) mixing a suspension of the inactivated virus envelope having membrane fusion activity and the stabilizer wherein the mixture has a total salt concentration of at most 3 mM; and (II) freeze-drying the mixture obtained in (1); and
   (2) bringing the composition obtained in (1) into contact with the cell or the living organism.

2. A cell fusion method, comprising:
   (a) rehydrating a freeze-dried composition containing an inactivated virus envelope having membrane fusion activity; wherein the inactivated virus envelope has membrane fusion activity, and at least one stabilizer selected from the group consisting of a protein hydrolysate, leucine, an L-arginine-acid and a polysaccharide, which is prepared by a process comprising (1) mixing a suspension of the inactivated virus envelope having membrane fusion activity and the stabilizer wherein the mixture has a total salt concentration of at most 3 mM; and (2) freeze-drying the mixture obtained in (1); and
   (b) mixing the composition obtained in (a) with a suspension of cells to be fused.

3. The method according to claim 1, wherein the inactivated virus envelope is an inactivated virus envelope of a virus of Paramyxoviridae, Orthomyxoviridae, Herpesviridae, Hepadnaviridae or Flaviviridae.

4. The method according to claim 1, wherein the stabilizer is a protein hydrolysate and a polysaccharide.

5. The method according to claim 1, wherein the concentration of the inactivated virus envelope in the mixture obtained in (1) corresponds to an OD of from 0.1 to 7.0.

6. The method according to claim 1, wherein the concentration of the protein hydrolysate, leucine or the L-arginine-acid in the mixture obtained in (1) is from 0.1 to 2.5%.

7. The method according to claim 4, wherein the concentration of the polysaccharide in the mixture obtained in (1) is from 0.05 to 0.5%.

8. The method according to claim 2, wherein the inactivated virus envelope is an inactivated virus envelope of a virus of Paramyxoviridae, Orthomyxoviridae, Herpesviridae, Hepadnaviridae or Flaviviridae.

9. The method according to claim 2, wherein the stabilizer is a protein hydrolysate and a polysaccharide.

10. The method according to claim 2, wherein the concentration of the inactivated virus envelope in the mixture obtained in (1) corresponds to an OD of from 0.1 to 7.0.

11. The method according to claim 2, wherein the concentration of the protein hydrolysate, leucine or the L-arginine-acid in the mixture obtained in (1) is from 0.1 to 2.5%.

12. The method according to claim 2, wherein the concentration of the polysaccharide in the mixture obtained in (1) is from 0.05 to 0.5%.

* * * * *